(12) United States Patent
Chang et al.

(10) Patent No.: US 6,294,309 B1
(45) Date of Patent: Sep. 25, 2001

(54) POSITIVE PHOTORESIST COMPOSITION CONTAINING ALICYCLIC DISSOLUTION INHIBITORS

(75) Inventors: Shang-Wern Chang, Taipei; Yen-Cheng Li, Sanchung; Shang-Ho Lin, Taipei; Wen-Chieh Wang, Chungho, all of (TW)

(73) Assignee: Everlight USA, Inc., Pineville, NC (US)

( * ) Notice: Subject to any disclaimer, the term of this patent is extended or adjusted under 35 U.S.C. 154(b) by 0 days.

(21) Appl. No.: 09/607,943

(22) Filed: Jun. 30, 2000

(51) Int. Cl.[7] ................................................ G03F 7/004
(52) U.S. Cl. ........................................ 430/270.1; 430/910
(58) Field of Search .............................. 430/270.1, 910

(56) References Cited

U.S. PATENT DOCUMENTS 6,045,967 * 4/2000 Jung et al. ..................... 430/270.1

FOREIGN PATENT DOCUMENTS

| 19860832-A | * | 7/1999 | (DE) . |
| 9-015846-A | * | 1/1997 | (JP) . |
| 9-265177-A | * | 10/1997 | (JP) . |

OTHER PUBLICATIONS

CA 134:56981.*
JPO abstract JP 09265177.*
CA 126:231536.*
CA 131:116681.*

* cited by examiner

Primary Examiner—Janet Baxter
Assistant Examiner—Rosemary Ashton
(74) Attorney, Agent, or Firm—Bacon & Thomas

(57) ABSTRACT

A positive photoresist composition comprising a polymer, a photoactived agent and an dissolution inhibitor represented by the following formula (1):

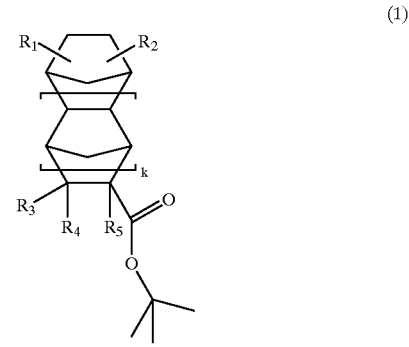

wherein $R_1$, $R_2$, $R_3$, $R_4$, $R_5$ and k are defined in the specification. The photoresist composition of the present invention is useful as a chemically amplified type resist when exposed to deep UV light from a KrF and ArF excimer laser.

15 Claims, No Drawings

POSITIVE PHOTORESIST COMPOSITION CONTAINING ALICYCLIC DISSOLUTION INHIBITORS

BACKGROUND OF THE INVENTION

1. Field of the Invention

The present invention relates to the lithography field, and more particularly to positive photoresist composition including dissolution inhibitors, and to dissolution inhibitors for such formulations.

2. Description of Related Art

Current semiconductor industry trends indicate that the development of high performance logic processors and 1-bit DRAM will require the availability of below 0.18 µm lithographic processes. In theory, two methods of forming finer resist patterns are to shorten the wavelength of an exposure light source and increase the numerical aperture (NA) of an exposure system.

Semiconductor industry implemented in manufacture of devices by deep UV lithography employing a KrF excimer laser (248 nm) stepper for 0.25 µm process. Due to the optical enhancement techniques such as high NA optical elements, phase shift mask, etc. The appearance of 248 nm KrF scanner offers the pilot-run of 0.18 µm process and development of below 0.15 µm process. However, there is a limit of wavelength shorten, the more difficult of mask produced. In order to minimize the device size, efforts to develop 193 nm (ArF excimer laser) lithography and resists have been tremendously accelerated in the last several years.

In addition to improved resolution, it is also desirable to provide positive resist materials having improved sensitivity. One approach to improving sensitivity uses the concept of chemical amplification. Chemical amplification involves the photogeneration within the resists of species that catalyze subsequent chemical events. One method of chemical amplification includes dissolution inhibition, wherein a masked phenol or protected carboxylic acid is mixed with a phenolic resin, resulting in a drastic decrease in the dissolution rate of the polymer in aqueous base developing solutions. A photoactivated acid-catalyzed deprotection reaction is then used to free the phenol or the carboxylic acid. As a result, the dissolution inhibitor is converted into a dissolution promoter in the radiation exposed areas of the resist material, allowing for the development of positive images.

There remains a need in the art for a positive photoresist composition having both high resolution and high sensitivity. There also remains a need in the art of composition for positive photoresist, which are useful in deep-UV image resolution techniques. Moreover, there remains a need in the art for positive photoresist dissolution inhibitors capable of providing high sensitivity.

SUMMARY OF THE INVENTION

The positive photoresist composition of the present invention comprises a polymer, a photoactived agent, and a dissolution inhibitor.

The dissolution inhibitor may be represented by the following formula (1):

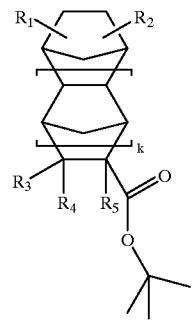

(1)

wherein $R_1$ and $R_2$ each independently is a hydroxyl group, a $C_{1-8}$ hydroxyalkyl group, or a $C_{3-8}$ hydroxycycloalkyl group; $R_3$, $R_4$ and $R_5$ each independently is a hydrogen, a $C_{1-8}$ hydroxyalkyl group, a $C_{1-6}$ carboxylic acid or a $C_{3-8}$ carboxylic acid ester; k is an integer of 0, 1, 2, 3, 4, 5 or 6. In such dissolution inhibitors, the compound of the formula (14) is preferred

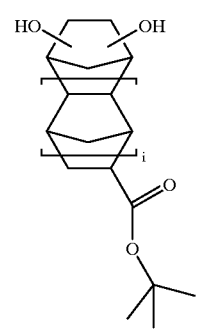

(14)

wherein i is 0 or 1.

DETAILED DESCRIPTION OF THE INVENTION

The positive photoresist composition of the present invention includes a polymer, a photoactived agent, and a dissolution inhibitor.

Suitable polymers for use in the present invention will be known to those skilled in the art. Preferably, the polymers will be transparent in at least a portion of the ultraviolet region of the electromagnetic spectrum. As used herein, the term "transparency" refers to a 500 µm thickness of polymer which essentially has an optical density of not more then 2.0 $um^{-1}$ in the wavelengths between about 190 nm and about 440 nm. Preferably, a 500 µm sample of the polymer has an optical density of not more than 2.0 $um^{-1}$ at one or more of the following wavelengths: 193 nm, 248 nm, 254 nm, and 365 nm.

Polymers which are useful in the present invention are generally soluble in an aqueous base solution after being UV irradiated. Any suitable polymers known to those skilled in the art may be employed in the practice of the present invention. Typically, suitable polymers contain a structure unit represented by the following formula (18), (19) or (20):

(18)
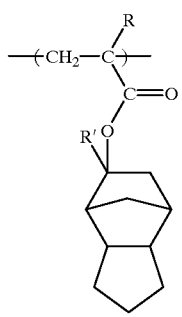
(19)
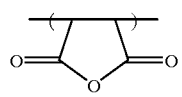
(20)
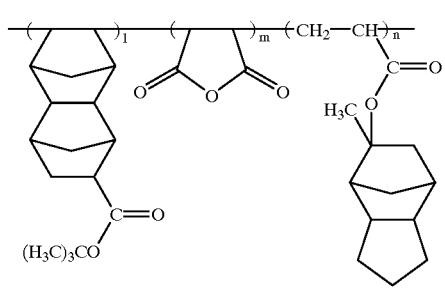
wherein R is a hydrogen or a $C_{1-4}$ alkyl group; R' is a hydrogen or a $C_{1-4}$ alkyl group.
Preferably, the above polymer is a polymer contains a structure unit selected from the following formula (21) to formula (29),
(21)
(22)
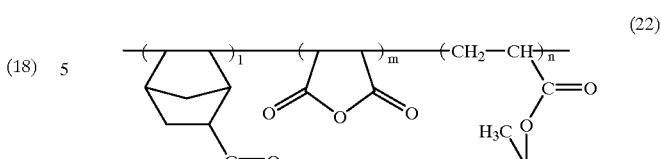
(23)
(24)
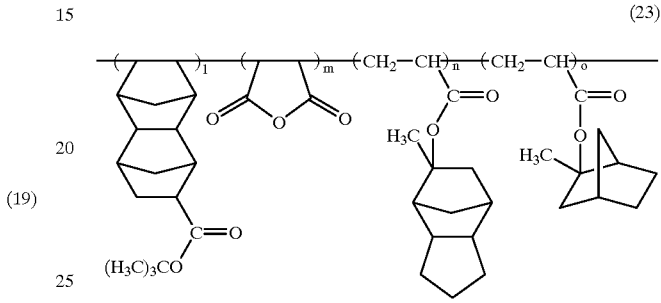
(25)
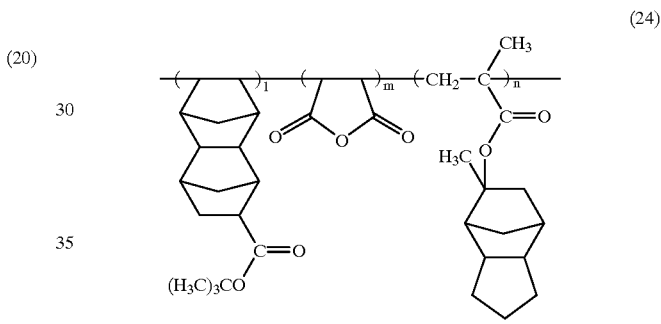
(26)
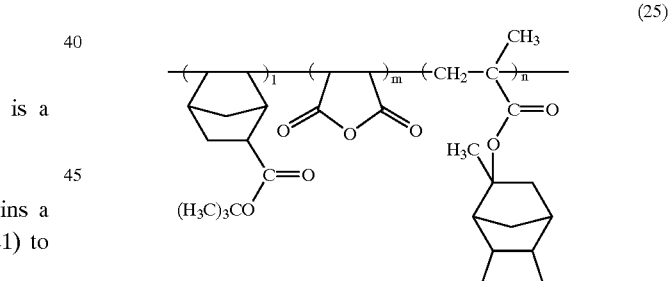
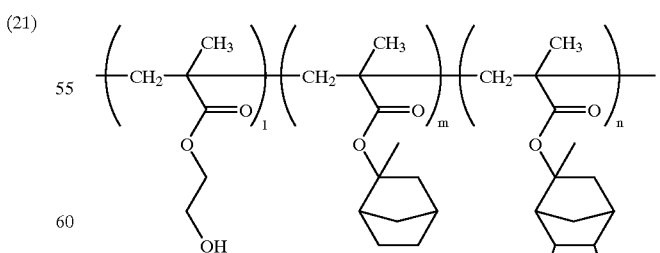

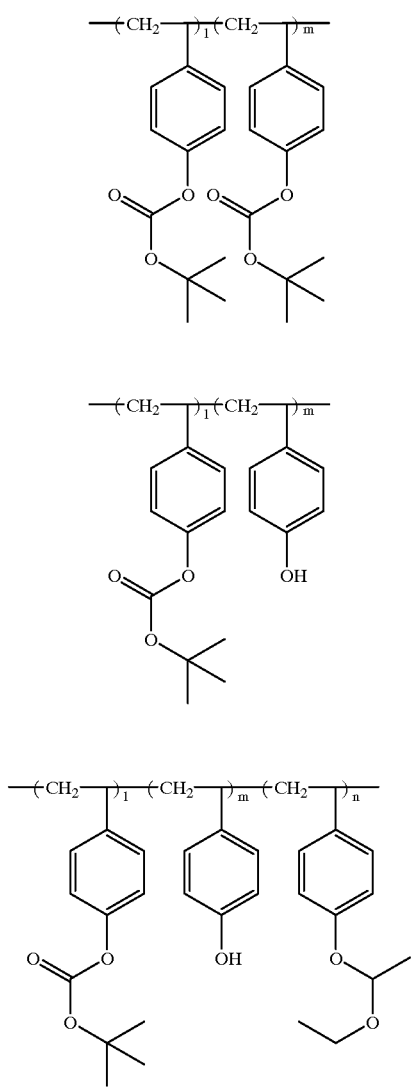

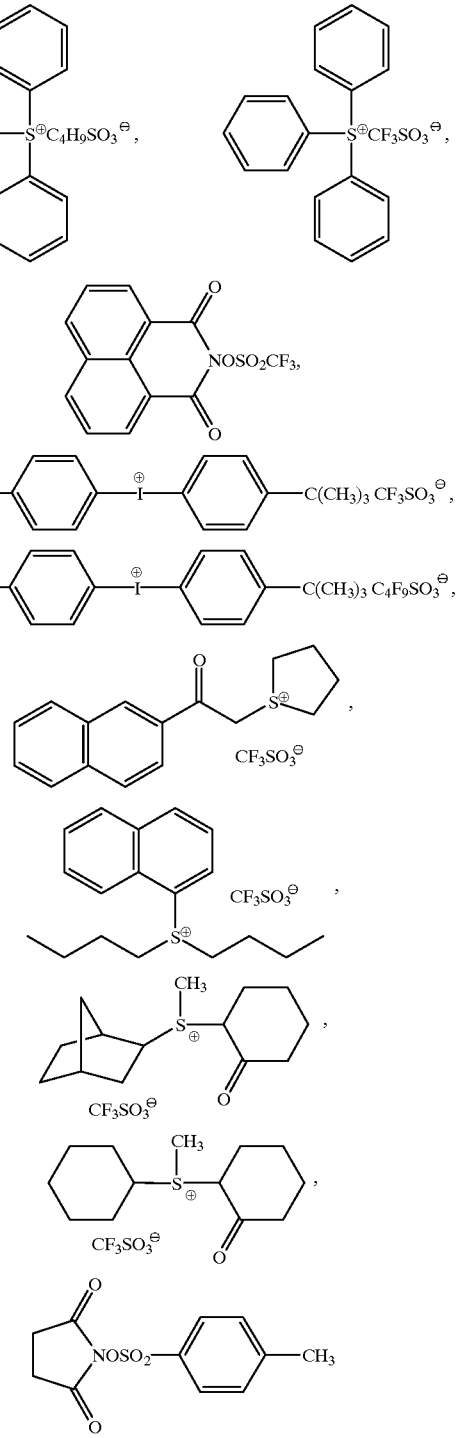

in the above structure unit of formula (21), (22), (24), (25), (26), and (29), wherein l+m+n=1, more preferably l/(l+m+n)=0.1–0.5, m/(l+m+n)=0.1–0.5, and n/(l+m+n)=0.1–0.5; in the above structure unit of formula (23), wherein l+m+n+o=1, more preferably l/(l+m+n+o)=0.1–0.5, m/(l+m+n+o)=0.1–0.5, n/(l+m+n+o)=0.1–0.5 and o/(l+m+n+o)=0.1–0.5; in the above structure unit of formula (27) and (28), wherein l+m=1, more preferably l/(l+m)=0.1–0.9, and m/(l+m)=0.1–0.9.

Any suitable photoactived agent known to those skilled in the art may be employed in the practice of the present invention. As used herein, the term "photoactived agent" refers to a compound whose chemical composition is altered upon exposure to radiation. Preferred photoactived agents include photoacid generators. Photoacid generators produce acid upon exposure to radiation. Photoacid generators, which are suitable for the present invention typically, produce strong acid upon exposure to radiation. There is no special limit to photoacid generators here. The photoacid generator suitable for the chemical amplified photoresist composition of the present invention meet the requirement to maintain stability before exposure. Preferably, suitable photoacid generators are:

The positive photoresist composition of the present invention can further include acid scavengers to adjust the diffusion of acid. Suitable acid scavengers can be

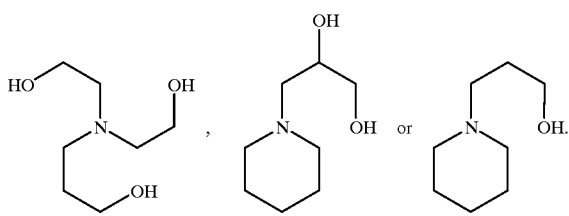

The photoresist further includes a dissolution inhibitor of the formula

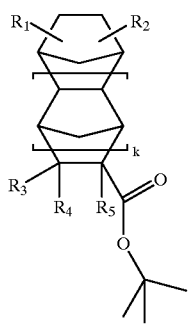

(1)

wherein $R_1$ and $R_2$ each independently is a hydroxyl group, a $C_{1-8}$ hydroxyalkyl group, or a $C_{3-8}$ hydroxycycloalkyl group; $R_3$, $R_4$ and $R_5$ each independently is a hydrogen, a $C_{1-8}$ hydroxyalkyl group, a $C_{1-6}$ carboxylic acid or a $C_{3-8}$ carboxylic acid ester; and k is an integer of 0, 1, 2, 3, 4, 5 or 6.

The ratio of each component of the present invention can be changed in wide a range. In general, the minimum relative weight percentage for each component is 1%, ant the maximum relative percentage is 98%. The composition of the present invention preferably contains polymer 10–98% by weight, photoactived agent 1–50% by weight, and dissolution inhibitor 1–50% by weight.

The positive photoresist composition of the present invention can be used to obtain chemical amplified photoresist. The positive photoresist of the present invention can be obtained by simply mixing the components together. There are no limits for the mixing methods. The positive photoresist composition of the present invention can be made by either adding other components into the solution of the photosensitive polymers (or copolymers) or adding the photosensitive polymers (or copolymers) into the solution of other components.

The impurities (e.g. trace amount of metal ions or halides) of the positive photoresist composition of the present invention should be removed as well as possible. The impurities in the components of the positive photoresist composition of the present invention can be removed before or after the components are mixed together.

The positive photoresist composition of the present invention can be used in the process of lithography. Especially, the positive photoresist composition of the present invention can be used in the process of 193 nm and 248 nm (ArF and KrF excimer laser) lithography. After the positive photoresist composition of the present invention is proceeded through normal lithographic procedures such as coating, exposure and development, patterns on substrates will form. As the positive photoresist composition of the present invention are used, the compositions are coated on a substrate first. Then the coating is baked to remove solvents, and exposed to a light source under masks to form patterns. The substrate used for 193 nm and 248 nm lithography here can be silicon or other materials. The coating methods to coat the positive photoresist composition of the present invention on substrates can be spin coating, spray coating and roll coating.

The developing solutions for the exposed resist coating can be ammonium, triethylamine, dimethylaminomethanol, hydroxylamine, sodium hydroxide, tetraethylammonium hydroxide, potassium hydroxide, sodium carbonate, potassium carbonate or trimethylhydroxylethylammonium hydroxide.

The resolution, shape, roughness and sensitivity of the positive photoresist composition of the present invention are good. In addition, the depth of focus, exposure border and removing border are excellent.

EXAMPLE 1

Preparation of trans-2,3-Dihydroxybicyclo[2.2.1] heptan-2-carboxylic acid tert-butyl Ester of the Formula (15)

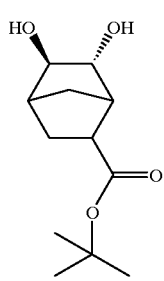

(15)

Bicyclo[2.2.1]heptan-3-ene-2-carboxylic acid tert-butyl ester (1.94 g) is dissolved in $CH_2Cl_2$ (20 mL). m-Chloroperoxybenzoic acid (2.7 g, 70%) was added and the mixture was stirred 24 hrs. When bicyclo[2.2.1]heptan-3-ene-2-carboxylic acid tert-butyl ester disappeared, $Na_2CO_3$(sat.) (20 mL) was added then stirred for an additional 2 hrs. The reaction mixture was extracted with ethyl acetate (20 mL×3). The combined organic layers were washed till the pH=7 then evaporated to dryness to obtain the 3-oxa-bicyclo[2.2.1]heptan-2-carboxylic acid tert-butyl ester.

3-Oxa-bicyclo[2.2.1]heptan-2-carboxylic acid tert-butyl ester (2.1 g) is dissolved in acetone (20 mL) and water (2 mL). Add $H_2SO_4$(conc.) until the pH=4 and stir for 48 hrs. When 3-oxa-bicyclo[2.2.1]heptan-2-carboxylic acid tert-butyl ester disappeared, $Na_2CO_3$ was added till pH=8. The reaction mixture was extracted with ethyl acetate (20 mL×3). The combined organic layers were washed till the pH=7 then evaporated to dryness. The crude product was purified by chromatography to obtain the trans-2,3-dihydroxybicyclo[2.2.1]heptan-2-carboxylic acid tert-butyl ester (Formula 15) as colorless needle crystal; mp=124.2° C.; $^1$H-NMR (CDCl$_3$, 300 MH) δ4.10–3.82 (2H, m), 2.54–2.51 (2H, m), 2.15–1.45 (4H, m), 1.43 (9H, s), 1.42–1.40 (1H, m); $^{13}$C-NMR (CDCl$_3$, 75 MHz) δ173.2, 80.5, 80.4, 75.3, 46.6, 44.7, 41.5, 34.4, 28.1, 24.0.

EXAMPLE 2

Preparation of cis-2,3-Dihydroxybicyclo[2.2.1] heptan-2-carboxylic acid tert-butyl Ester of the Formula (16)

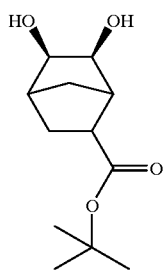

(16)

Bicyclo[2.2.1]heptan-3-ene-2-carboxylic acid tert-butyl ester (1.94 g) is dissolved in acetone (50 mL). Dissolving potassium permanganate (2.37 g) in water (10 mL) was added at 0° C. and the mixture was stirred under N$_2$ at 0° C. for 45 min. Sodium hydroxide (6.0 g) was dissolved in water (10 mL) and added to the reaction mixture at 0° C. then stirred for an additional 12 hrs at room temperature. Evaporate the acetone from the filtrate, then extracted with ethyl acetate (20 mL×3). The combined organic layers were washed till the pH=7 and evaporated to dryness. Purif by silica gel column chromatography to give cis-2,3-dihydroxybicyclo[2.2.1]heptan-2-carboxylic acid tert-butyl ester (Formula 16) as colorless needle crystal; mp=83.1° C.; $^1$H-NMR (CDCl$_3$, 300 MHz) δ3.82 (1H, m), 3.68 (1H, m), 2.6–1.50 (6H, m), 1.38 (9H, s), 1.17 (1H, m); $^{13}$C-NMR (CDCl$_3$, 75 MHz) δ173.6, 80.7, 73.8, 70.4, 46.7, 43.7, 43.6, 33.5, 28.1, 27.2.

EXAMPLE 3

Preparation of cis-3,4-Dihydroxytetracyclo[4.4.0.1$^{2,5}$0.1$^{7,10}$]dodec-8-carboxylic acid tert-butyl Ester of the Formula (17)

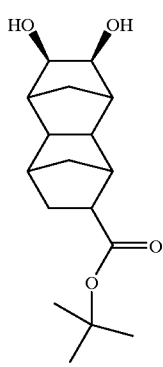

(17)

Tetracyclo[4.4.0.1$^{2,5}$0.1$^{7,10}$]dodec-3-ene-8-carboxylic acid tert-butyl ester (2.60 g) is dissolved in acetone (50 mL). Dissolving potassium permanganate (2.37 g) in water (10 mL) was added at 0° C. and the mixture was stirred under N$_2$ at 0° C. for 45 min. Sodium hydroxide (6.0 g) was dissolved in water (10 mL) and added to the reaction mixture at 0° C. then stirred for an additional 12 hrs at room temperature. Evaporate the acetone from the filtrate then extracted with ethyl acetate (20 mL×3). The combined organic layers were washed till the pH=7 and then evaporated to dryness. Purif by silica gel column chromatography to give cis-3,4-dihydroxytetracyclo[4.4.0.1$^{2,5}$0.1$^{7,10}$]dodec-8-carboxylic acid tert-butyl ester (Formula 17) as colorless oil; $^1$H-NMR (CDCl$_3$, 300 MHz) δ4.18 (2H, br s), 2.60–1.51 (9H, m), 1.39 (9H, s), 1.29–1.01 (4H, m).

EXAMPLE 4

Synthesis of Polymer (21)

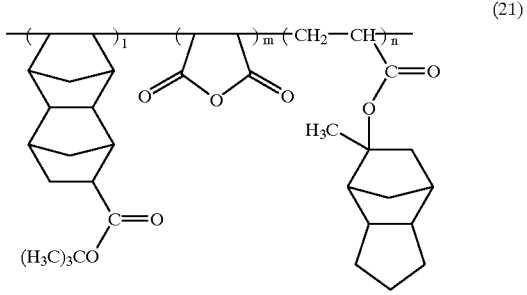

(21)

wherein: l+m+n=1.

The initiator (4.92 g, 2,2'-azo-bis-isobutyronitrile; AIBN) is added to the mixture of tetrahydrofuran (60 ml), tert-butyl tetracyclo[4.4.0.1$^{2,5}$0.1$^{7,12}$]dodec-3-ene-5-carboxylate (26 g), 8-methyl tricyclo[5.2.1.0$^{2,6}$]decan-8-yl acryloylate(23.4 g) and maleic anhydride (9.8 g), then the mixture is heated to 70° C. and stirred overnight. Tetrahydrofuran (20 ml) is added to the mixture. After the resultant product mixture (20 ml) is added to 1 l of hexane, dropwise and slowly, a white solid precipitate is obtained. The white solid is collected by filtration and dried to yield 30.23 g (51%) of the polymer (21), weight-average molecular weight 10875 (measured by GPC), glass transition temperature Tg=183° C., degradation temperature Td=212° C.

EXAMPLE 5

Synthesis of Polymer (24)

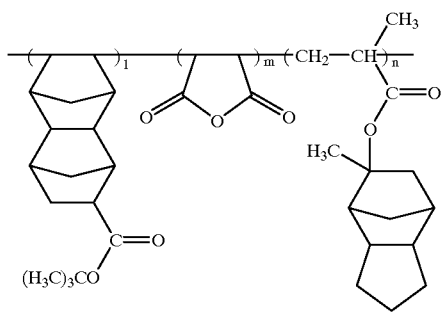

wherein: l+m+n=1.

The initiator (4.92 g, 2,2'-azo-bis-isobutyronitrile; AIBN) is added to the mixture of tetranydrofuran (60 ml), tert-butyl tetracyclo[4.4.0.1$^{2,5}$0.1$^{7,12}$]dodecan-3-ene-5-carboxylate (26 g), 8-methyl tricyclo[5.2.1.0$^{2,6}$]decan-8-yl acryloylate (23.4 g) and maleic anhydride (9.8 g). Then the mixture is heated to 70° C. and stirred overnight. Tetrahydrofuran (20 ml) is added to the mixture. After 20 ml of the resultant mixture is added to 1 l of hexane, dropwise and slowly, a white solid precipitate is obtained. The white solid is collected by filtration and then dried to yield 28.89 g (32%) of polymer (24), weight-average molecular weight 29810 (measured by GPC), glass transition temperature Tg=178° C., degradation temperature Td=209° C.

EXAMPLE 6

Photoresist Compositions

Triphenylsulfonium perfluoro-1-butanesul-fonate (TPS-PFBS, 0.05 g), trans-2,3-dihydroxybi cyclo[2.2.1]heptan-2-carboxylic acid tert-butyl ester (Formula 15) (0.06 g), propylene glycol monomethyl ether acetate (10.4 g), polymer (21) (2.0 g) and trioctylamine (0.5 mg) are mixed together and filtered by a 0.45 μm filter. The resultant solution is spin coated on a silicon substrate by 2200 rpm for 30 sec.

The coated substrate is dried at 130° C. for 90 seconds. The thickness of the coating is 436.8 nm. The resists films were exposed using an ISI 193 nm Microstepper (0.6 NA, 0.7 σ) then baked on a heating plate at 130° C. for 90 sec.

The exposed coating is developed by an aqueous solution of 2.38% tetramethyl ammonium hydroxide (TMAH). After the coated substrate is washed by deionized water and dried, the exposed area shows a structure of resolution of 0.13 μm under the observation of a scanning electronic microscopy (SEM)

EXAMPLE 7 to 10 & COMPARATIVE EXAMPLE 1 to 4

Example 6 is repeated using different polymer or dissolution inhibitor as table 1, and the resolution also are shown in table 1.

TABLE 1

| | Polymer | Dissolution Inhibitor | Thickness of film (nm) | Resolution (μm) |
|---|---|---|---|---|
| Example 6 | formula (2) | formula (11) | 421.5 | 0.13 |
| Example 7 | formula (2) | formula (12) | 385.2 | 0.13 |
| Example 8 | formula (2) | formula (13) | 452.3 | 0.14 |
| Example 9 | formula (2) | formula (13) | 412.2 | 0.14 |
| Example 10 | formula (5) | formula (12) | 448.3 | 0.13 |
| Comparative Example 1 | formula (2) | — | 421.5 | 0.15 |
| Comparative Example 2 | formula (5) | — | 398.7 | 0.20 |
| Comparative Example 3 | formula (2) | t-butyl cholate | 432.1 | 0.15 |
| Comparative Example 4 | formula (5) | t-butyl cholate | 443.2 | 0.16 |

The positive photoresist compositions of the present invention can be used in lithography, especially 193 nm and 248 nm lithography. The resolution, roughness, and shape of the resist pattern formed from the positive photoresist composition of the present invention dissolution inhibitor are more excellent than the comparative examples.

From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A positive photoresist composition comprising a polymer, a photoactived agent and a dissolution inhibitor represented by the following formula (1):

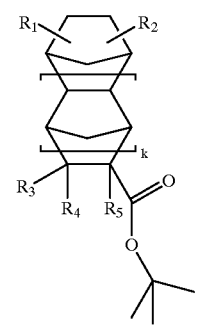

wherein:
   $R_1$ and $R_2$ each independently is a hydroxyl group, a $C_{1-8}$ hydroxyalkyl group, or a $C_{3-8}$ hydroxycycloalkyl group;
   $R_3$, $R_4$ and $R_5$ each independently is a hydrogen, a $C_{1-8}$ hydroxyalkyl group, a $C_{1-6}$ carboxylic acid or a $C_{3-8}$ carboxylic acid ester; and
   k is an integer of 0, 1, 2, 3, 4, 5 or 6.

2. The positive photoresist composition of claim 1, wherein said polymer is essentially transparent in at least a portion of the ultraviolet region of the electromagnetic spectrum.

3. The positive photoresist composition of claim 1, wherein said polymer includes a structure unit represented by the following formula (18)

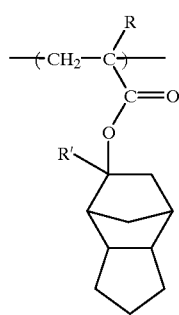

(18)

wherein:
R is a hydrogen or a $C_{1-4}$ alkyl group; R' is a hydrogen or a $C_{1-4}$ alkyl group.

4. The positive photoresist composition of claim 1, wherein said polymer includes a structure unit represented by the following formula (19)

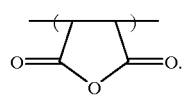

(19)

5. The positive photoresist composition of claim 1, wherein said polymer includes a structure unit represented by the following formula (20)

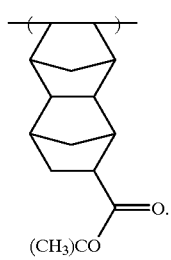

(20)

6. The positive photoresist composition of claim 1, wherein said polymer includes a structure unit represented by the following formula (21)

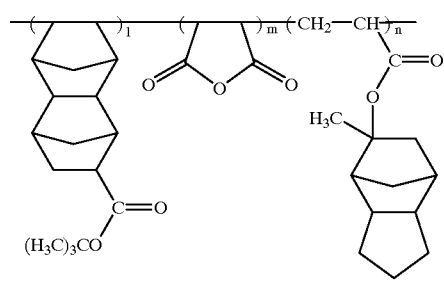

(21)

wherein: l+m+n=1.

7. The positive photoresist composition of claim 6, wherein l/(l+m+n)=0.1 to 0.5, m/(l+m+n)=0.1 to 0.5, or n/(l+m+n)=0.1 to 0.5.

8. The positive photoresist composition of claim 1, wherein said polymer includes a structure unit represented by the following formula (24)

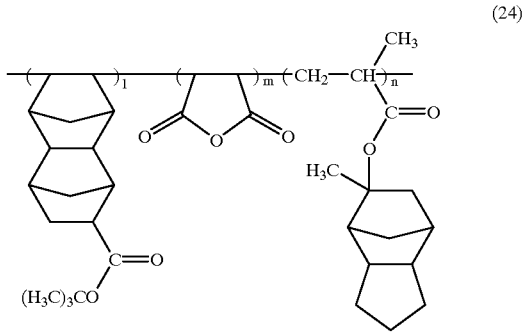

(24)

wherein: l+m+n=1.

9. The positive photoresist composition of claim 8, wherein l/(l+m+n)=0.1 to 0.5, m/(l+m+n)=0.1 to 0.5, or n/(l+m+n)=0.1 to 0.5.

10. The positive photoresist composition of claim 1, wherein said polymer has a weight average molecular weight ranging from 1,000 to 500,000.

11. The positive photoresist composition of claim 1 comprising polymer 10–98% by weight, photoactived agent 1–50% by weight and dissolution inhibitor 1–50% by weight.

12. The positive photoresist composition of claim 1, wherein said dissolution inhibitor is represented by the following formula (14):

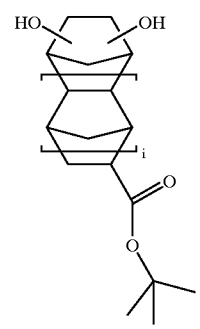

(14)

wherein: i is 0 or 1.

13. The positive photoresist composition of claim 12, wherein said dissolution inhibitor is the following formula (15):

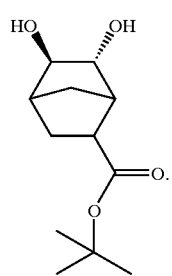
(15)
14. The positive photoresist composition of claim 12, wherein said dissolution inhibitor is the following formula (16):
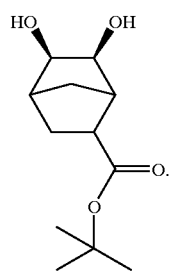
(16)
15. The positive photoresist composition of claim 12, wherein said dissolution inhibitor is the following formula (17):
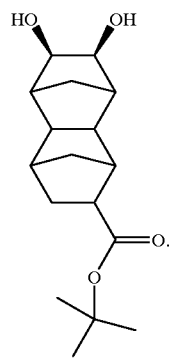
(17)
* * * * *